(12) United States Patent  
Rodenfels et al.

(10) Patent No.: US 8,916,110 B2  
(45) Date of Patent: Dec. 23, 2014

(54) APPARATUS AND METHOD FOR SEPARATING CONSTITUENT PARTS OF A SAMPLE LIQUID

(75) Inventors: Tobias Rodenfels, Dortmund (DE); Gert Blankenstein, Arlington, MA (US)

(73) Assignee: Boehringer Ingelheim Microparts GmbH, Dortmund (DE)

( * ) Notice: Subject to any disclaimer, the term of this patent is extended or adjusted under 35 U.S.C. 154(b) by 0 days.

(21) Appl. No.: 13/811,729

(22) PCT Filed: Jul. 5, 2011

(86) PCT No.: PCT/EP2011/061297  
§ 371 (c)(1),  
(2), (4) Date: Mar. 22, 2013

(87) PCT Pub. No.: WO2012/019828  
PCT Pub. Date: Feb. 16, 2012

(65) Prior Publication Data  
US 2013/0209331 A1    Aug. 15, 2013

(30) Foreign Application Priority Data

Jul. 27, 2010  (EP) .................................... 10007766  
Dec. 16, 2010  (EP) .................................... 10015721

(51) Int. Cl.  
*G01N 21/75* (2006.01)  
*B01D 61/38* (2006.01)  
(Continued)

(52) U.S. Cl.  
CPC ........ *B01D 61/38* (2013.01); *G01N 2021/0346* (2013.01); *G01N 33/86* (2013.01);  
(Continued)

(58) Field of Classification Search  
CPC .................... G01N 2021/0346; G01N 33/491; G01N 33/5302; G01N 33/86; B01L 2200/027; B01L 2300/043; B01L 2400/0406; B01L 2400/086  
USPC ......... 422/400, 401, 412, 420, 421, 422, 423, 422/424, 425, 426, 427, 428, 429, 534, 947, 422/68.1, 82.05, 82.06; 436/164, 169, 170; 435/13, 283.1, 287.1, 287.7, 287.8, 435/287.9, 288.7  
See application file for complete search history.

(56) References Cited

U.S. PATENT DOCUMENTS 3,799,742 A    3/1974  Coleman  
6,019,944 A    2/2000  Buechler  
(Continued)

FOREIGN PATENT DOCUMENTS

FR    2929135        10/2009  
WO    9723780 A1     7/1997  
(Continued)

OTHER PUBLICATIONS

International Search Report, Form PCT/ISA/210, for corresponding PCT/EP2011/061297; date of mailing: Jan. 26, 2012.

*Primary Examiner* — Dennis M White  
(74) *Attorney, Agent, or Firm* — Michael P. Morris; Mary-Ellen M. Devlin (57) ABSTRACT

A device and a process are proposed for separating constituents of a sample fluid, wherein the sample fluid is supplied by capillary force to a receiving region (7) for metering, stopping or delaying the sample fluid and the sample fluid is pre-treated with a soluble chemical (13) in the receiving region (7) before the sample fluid is supplied to a separating device (5) for separating off constituents of the sample fluid.

11 Claims, 6 Drawing Sheets

(51) Int. Cl.
*B01L 3/00* (2006.01)
*G01N 33/49* (2006.01)
*G01N 21/03* (2006.01)
*G01N 33/86* (2006.01)
*G01N 33/53* (2006.01)

(52) U.S. Cl.
CPC ...... *G01N 33/5302* (2013.01); *B01L 3/502715* (2013.01); *B01L 3/502753* (2013.01); *B01L 2200/027* (2013.01); *B01L 2200/0621* (2013.01); *B01L 2300/043* (2013.01); *B01L 2300/047* (2013.01); *B01L 2300/0681* (2013.01); *B01L 2300/0887* (2013.01); *B01L 2400/0406* (2013.01); *B01L 2400/0633* (2013.01); *B01L 2400/0688* (2013.01); *B01L 2400/086* (2013.01); *G01N 33/491* (2013.01)
USPC ........... 422/412; 422/400; 422/401; 422/420; 422/421; 422/422; 422/423; 422/424; 422/425; 422/426; 422/427; 422/428; 422/429; 422/947; 422/68.1; 422/82.05; 422/82.06; 436/164; 436/169; 436/170; 435/13; 435/283.1; 435/287.1; 435/287.7; 435/287.8; 435/287.9; 435/288.7

(56) References Cited

U.S. PATENT DOCUMENTS

| 6,106,732 | A  | * | 8/2000 | Johnston et al. .............. 210/767 |
| 2006/0105469 | A1 | | 5/2006 | Lea |
| 2011/0011781 | A1 | * | 1/2011 | Blankenstein et al. ....... 210/205 |
| 2011/0124984 | A1 | | 5/2011 | Rostaing |
| 2013/0209331 | A1 | | 8/2013 | Rodenfels |

FOREIGN PATENT DOCUMENTS

| WO | 2007057744 | A2 | 5/2007 |
| WO | 2007099344 | | 9/2007 |
| WO | 2009106331 | A2 | 9/2009 |

* cited by examiner

APPARATUS AND METHOD FOR SEPARATING CONSTITUENT PARTS OF A SAMPLE LIQUID

The present invention relates to a device for separating constituents of a sample fluid, particularly blood, according to the precharacterising clause of claim 1 and a process relating thereto.

The present invention relates particularly to microfluidic systems or devices. The following remarks therefore preferably refer to devices and processes in which capillary forces come into effect and in particular are critical to the function. Preferably, however, the present invention may also be used in other, particularly pressure-operated devices and processes.

A microfluidic device for plasma separation is known for example from WO 2009/106331 A2.

The present invention is based on the problem of providing a device and a process for separating constituents of a sample fluid, enabling simple pre-treatment of the test liquid by at least one chemical in the device before contact with a separating device and/or simple metering of the sample fluid that is to be added.

The above problem is solved by a device according to claim 1 or a process according to claim 15. Advantageous further features are the subject of the sub-claims.

A device as proposed comprises a receiving device which in turn comprises a receiving region for metering, stopping or delaying the sample fluid by capillary force and/or a chemical that can be dissolved by the sample fluid for pre-treating the sample fluid before it is fed to a separating device. Particularly preferably it is a chemical that is dried on in the receiving region and is dissolved by the sample fluid before it is fed to the separating device. The receiving region is preferably configured for metering, stopping or delaying the sample fluid by capillary force. The receiving region can also be used in particular in pressure-operated systems, devices or processes. Thus the sample fluid can very easily be pre-treated by the chemical before the actual separation. In particular, the pre-treatment may be carried out in a more defined manner than is the case when the chemical is integrated in the separating device or a filter element of the separating device.

Particularly preferably, the receiving device or its receiving region comprises a sloping ramp with an associated cover or a plurality of elevations which form a field of columns, in particular. This is a very simple way of providing the desired metering, stopping or delaying of the sample fluid by capillary force.

It should be noted that the receiving device or the receiving region with the sloping ramp and/or a plurality of elevations that form a field of columns, in particular, may optionally also be produced or used separately from a separating device or the separation of constituents from the sample fluid, in particular in order to stop, delay and/or meter the sample fluid. Generally, the present invention thus relates in particular to the manipulation of a sample fluid and is particularly preferably not limited to the separation of constituents out of the sample fluid.

The proposed process is particularly characterised in that the sample fluid is taken into the microfluidic device and there it is pre-treated with a chemical in a receiving region of the device separate from the separating device and only after the pre-treatment is it passed on to the separating device for separating constituents out of the pre-treated sample fluid. This in turn allows a very simple pre-treatment, while spatial and temporal separation of the pre-treatment from the preferred subsequent separation of constituents of the pre-treated sample fluid ensures a particularly efficient and/or defined progress of the process and/or a particularly efficient separation of constituents from the pre-treated sample fluid.

Further advantages, features, properties and aspects of the present invention will become apparent from the claims and the following description of preferred embodiments by reference to the drawings, wherein:

In the figures, the same reference numerals are used for identical or similar parts, where corresponding or comparable properties and advantages are obtained even if the description is not repeated.

Figure 1:
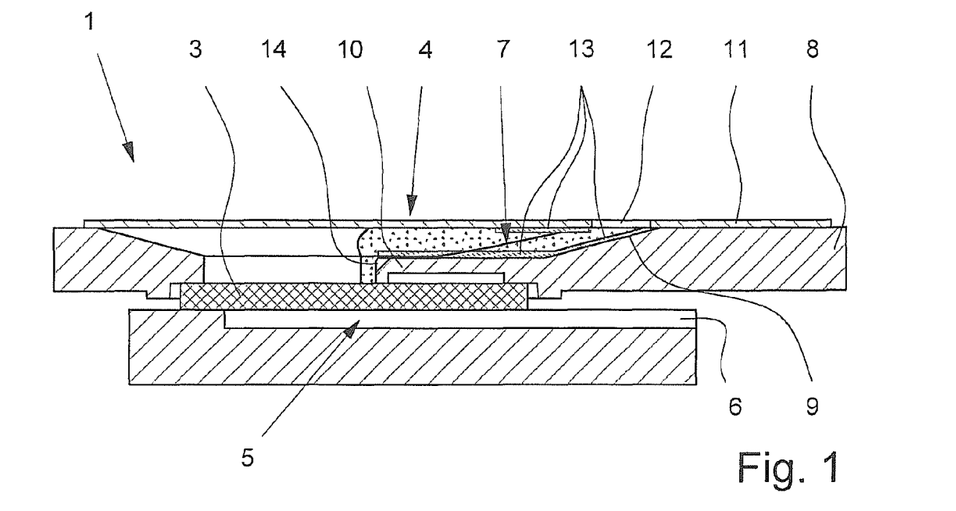
FIG. 1 is a schematic section through a proposed device according to a first embodiment.

FIG. 1 shows, in schematic section, a first embodiment of a proposed device 1 for the manipulation of a sample fluid 2, preferably for separating constituents of the sample fluid 2, especially blood or some other human or animal body fluid. In particular, the device 1 is used for separating off blood constituents such as blood cells.

Preferably, the device 1 for separating off constituents comprises a separating device 3, as indicated in FIG. 1. The separating device 3 preferably comprises a membrane or other suitable filter element. The membrane or the filter element may if necessary be of multilayered construction. For example, the separating device 3 or the membrane may be embodied as described in WO 2009/106331 A2, which is thus incorporated by reference as a supplementary disclosure.

The separating device 3 is preferably provided only optionally. In particular, the separating device 3 may also be omitted, particularly preferably if the device 1 or the proposed process is designed or used for the general manipulation of the sample fluid 2 and/or for metering the sample fluid 2.

The device 1 comprises a receiving device 4 for receiving the sample fluid 2 and preferably a particularly microfluidic structure 5, downstream of the separating device 3, for draining the sample fluid 2 away after the removal of constituents.

The holding capacity of the device 1 or of individual components such as the receiving device 4, separating device 3 and/or structure 5, is preferably less than 1 mm, particularly less than 500 µl, particularly preferably less than 100 µl.

The receiving device 4, the separating device 3 and the structure 5 are preferably arranged above one another, particularly at least substantially on opposite flat sides of the preferably planar separating device 3.

In the embodiment shown the structure 5 preferably comprises a channel 6 for draining away sample fluid 2 after the removal of constituents by the separating device 3. The channel 6 or a chamber formed thereby adjoins the separating device 3 particularly on the outflow side and conveys the sample fluid 2 for example to another structure, an investigating region or the like, which may also be formed by the device 1. In particular, the device 1 may therefore also be used for the investigation and, for example, measurement of analytes or other values of the sample fluid 2.

The receiving device 4 comprises a receiving region 7 for metering, stopping and/or delaying the sample fluid 2, particularly by capillary force. The receiving region 7 is preferably arranged upstream of, above and/or on the separating device 3.

Alternatively it is also possible that the receiving device 4 or the receiving region 7 is arranged downstream of or below the separating device 3 or is arranged after it. In this case the receiving device 4 or the receiving region 7 may in particular hold back the sample fluid 2 released from the separating device 3, in this case preferably filtered sample fluid 2, until for example a certain amount of sample fluid 2 has been separated or released by the separating device 3 and/or has accumulated in the receiving device 4 or in the receiving region 7. The sample fluid 2 can then be released for example to the adjoining structure 5.

In the embodiment shown, the device 1, the separating device 3 or the receiving device 4 comprises a carrier 8 which holds or carries the separating device 3, in particular, and/or preferably forms, holds and/or delimits the receiving device 4 or its receiving region 7. However, other design solutions are also possible.

The carrier 8 is preferably of plate-shaped and/or flat configuration.

The receiving region 7 in the embodiment shown preferably comprises a sloping ramp 9 and/or a guide region 10. In the embodiment shown, the ramp 9 and the guide region 10 are preferably formed by the carrier 8 or supported by it.

The receiving region 7 or the ramp 9 and/or the guide region 10 is or are preferably arranged above or over the separating device 3 and/or extend over it. In the embodiment shown, the guide region 10 preferably extends at a spacing from or above the separating device 3. In particular the guide region 10 is disposed in the manner of a plateau above the separating device 3 or at a spacing from it. Preferably, the guide region 10 is formed by a wall facing the receiving region 7, pointing upwards in the representation shown in FIG. 1.

The receiving region 7 or the ramp 9 and/or the guide region 10 is or are covered—at least partly—by an associated cover 11. The cover 11 is preferably embodied as a foil or film and may be formed for example by an adhesive film or laminated film or the like. In the embodiment shown, the cover 7 is held by the carrier 8. However, other design solutions are also possible. For example, a solid lid may also be used as the cover 7.

The receiving region 7 is preferably formed between the ramp 9 and/or the guide region 10 on the one hand and the cover 11 on the other hand.

For filling with or receiving the sample fluid 2, the receiving device 4 or the cover 11 preferably comprises a receiving opening 12 which is shown in FIG. 1.

The receiving opening 12 is preferably disposed adjacent to the ramp 9 and, more particularly, at its upper end or start.

The receiving region 7 is preferably configured such that during filling with the sample fluid 2 the liquid is initially stopped or delayed in the receiving region 7. This is achieved in the embodiment shown in particular by the fact that the sample fluid 2 is initially held back very forcefully between the ramp 9 and the associated cover 11 and from there slowly fills the receiving region 7 until the guide region 10 is at least substantially filled with the sample fluid 2 or until, in the representation shown in FIG. 1, the liquid front reaches the left-hand end region of the receiving region 7, as shown in FIG. 1.

The filling of the receiving region 7 with the sample fluid 2 is preferably visible to the user. The cover 11 is of transparent construction, for example, for this purpose. When the receiving region 7 is full the user can tell that sufficient sample fluid 2 has been taken in. The receiving device 4 and its receiving region 7 thus serve to assist with the metering of the sample fluid 2, in particular.

Figure 2:
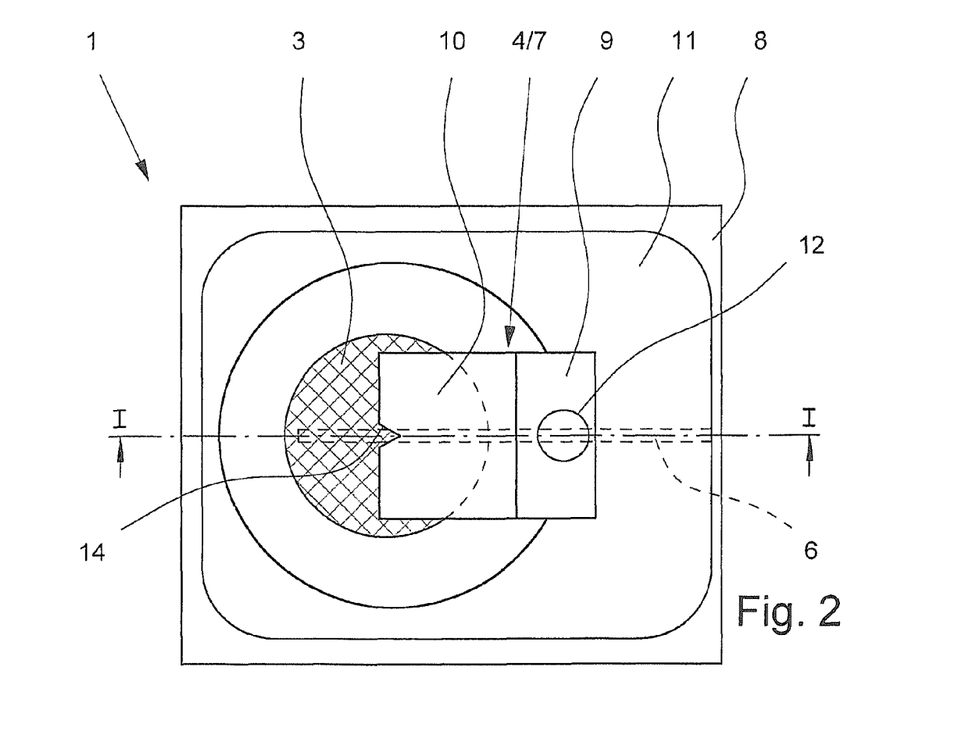
FIG. 2 is a plan view of the device according to FIG. 1.

FIG. 2 shows in schematic plan view the device 1, with the cover 11 shown as transparent, while the sample fluid 2 has been omitted for the purposes of the illustration. FIG. 1 shows a section along the line I-I in FIG. 2.

The receiving device 4 or its receiving region 7 preferably comprises a chemical 13 for pre-treatment of the sample fluid 2 before it is fed to the separating device 3. The chemical 13 is schematically shown in FIG. 1 as a coating that is provided particularly in the receiving region 7, preferably on the ramp 9, the guide region 10 and/or the cover 11, as schematically shown in FIG. 1.

The chemical 13 is in particular a dry chemical or dried-on chemical. The chemical 13 is dissolved by the sample fluid 2 and can then react with the sample fluid 2 for the pre-treatment. This is proposed to take place before the sample fluid 2 is supplied to the separating device 3.

According to one embodiment, the chemical 13 contains an agglutinating agent or is formed thereby. This assists with or brings about the clumping together or agglomeration particularly of blood cells or the like when blood is taken up as the sample fluid 2. This helps with the subsequent separation of blood cells in the separating device 3. Tests have shown that this results in a substantially better throughput of the sample fluid 2 through the separating device 3.

According to another embodiment the chemical 13 preferably contains or is formed by a clotting inhibitor or other agent that brings about or promotes deagglomeration. This, too, can be used to positively influence the subsequent separation of constituents, particularly blood constituents, from the sample fluid 2 in the separating device 3.

After the pre-treatment of the sample fluid 2 it is passed on to the separating device 3. In the first embodiment shown this preferably takes place through a fluidic connection between the receiving device 4 or receiving region 7 on the one hand and the separating device 3 on the other hand. In the embodiment shown, the fluidic connection is embodied in particular as a throttle connection for constricted conveying of sample fluid 2 from the receiving region 7 to the separating device 3. Particularly preferably, the fluidic connection is formed by a channel, a groove 14 or the like, which preferably connects the receiving region 7 or guide region 10 to the separating device 3, as shown schematically in FIGS. 1 and 2.

The fluidic connection is preferably arranged on or attached to the receiving region 7 at a different end from the receiving opening 12, so that it conveys the sample fluid 2—preferably slowly or in throttled manner—to the separating device 3 only after the receiving region 7 has been at least substantially completely filled with the sample fluid 2.

In the embodiment shown the fluidic connection supplies the sample fluid 2 that has preferably been pre-treated in the receiving device 4 or in the receiving region 7 to the separating device 3 at the receiving end, particularly at least substantially in the centre thereof. If necessary, a number of fluidic connections may be formed to the separating device 3, in order in particular to supply the sample fluid 2 to the separating device 3 at different points or regions.

According to one embodiment it is also possible for the fluidic connection to be at least temporarily blocked or barred initially by the chemical 13 or by a different, additional chemical or a so-called time control member or the like, in order to ensure a specified, certain or predetermined pre-treatment time for the sample fluid 2 in the receiving device 4 or in the receiving region 7.

FIG. 1 shows how the sample fluid 2 already flows through the fluidic connection from the receiving region 7 centrally—in this case through the groove 14—to the separating device 3. Then, in the separating device 3, constituents of the sample fluid 2, particularly blood cells or the like, are separated off. The sample fluid 2 flows at least substantially in the direction of thickness through the separating device 3, but the sample fluid 2 is also distributed in particular over the surface of the entry side of the separating device 3.

After the separation of constituents, the sample fluid 2 is taken up and carried away by the structure 5 or its channel 6 or the like. This is not shown in FIG. 1.

The sample fluid 2 is held in the receiving region 7 or on the ramp 9 and particularly on the guide region 10, preferably by capillary force, against an undefined, lateral outflow onto the separating device 3. This is preferably achieved, in particular in the embodiment shown, by a comparatively small spacing from the cover 11 of, for example, less than 100 μm. However, in principle, other distances or spacings are also possible, for example several millimeters.

Some additional embodiments of the proposed device 1 will now be described with reference to the other figures, while only major differences from the first embodiment will be explained. The remarks and explanations provided hereinbefore are therefore of complementary or corresponding relevance, even if the associated description has not been repeated.

Figure 3:
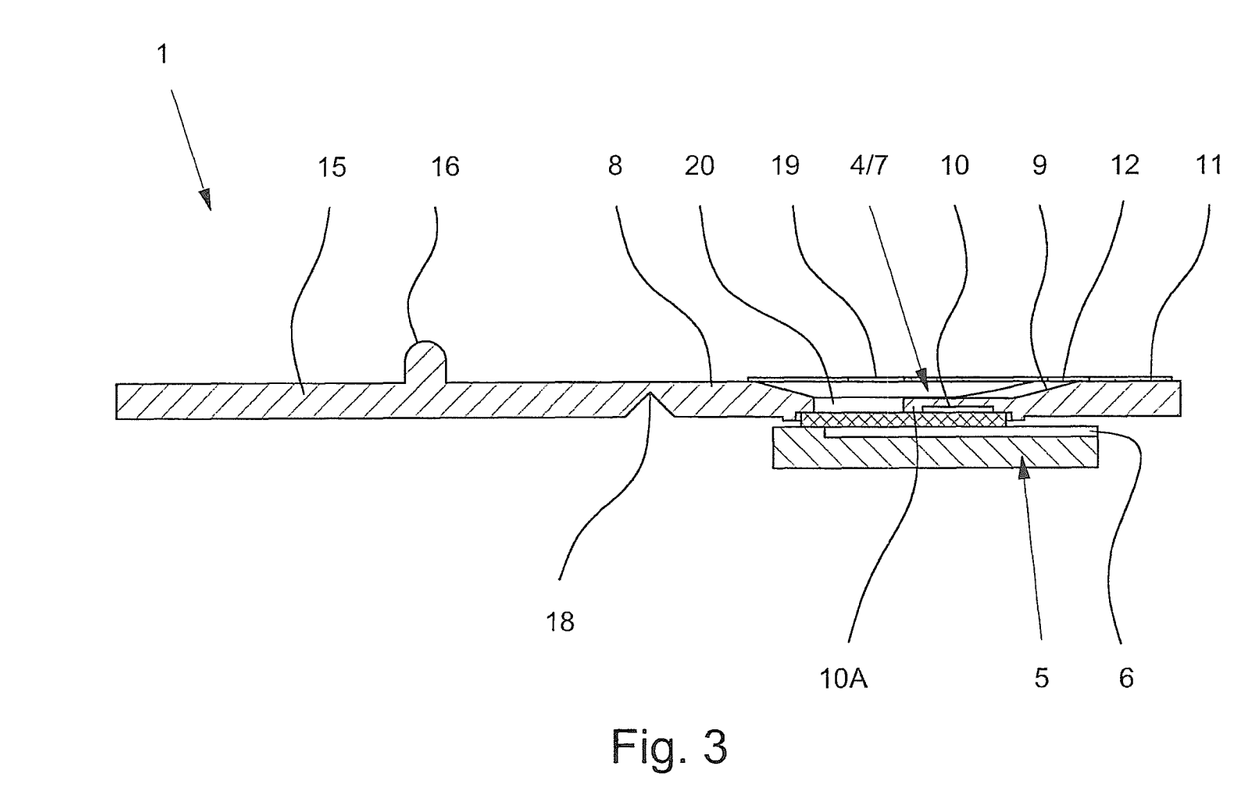
FIG. 3 is a schematic section through a proposed device according to a second embodiment, with the lid open.
Figure 4:
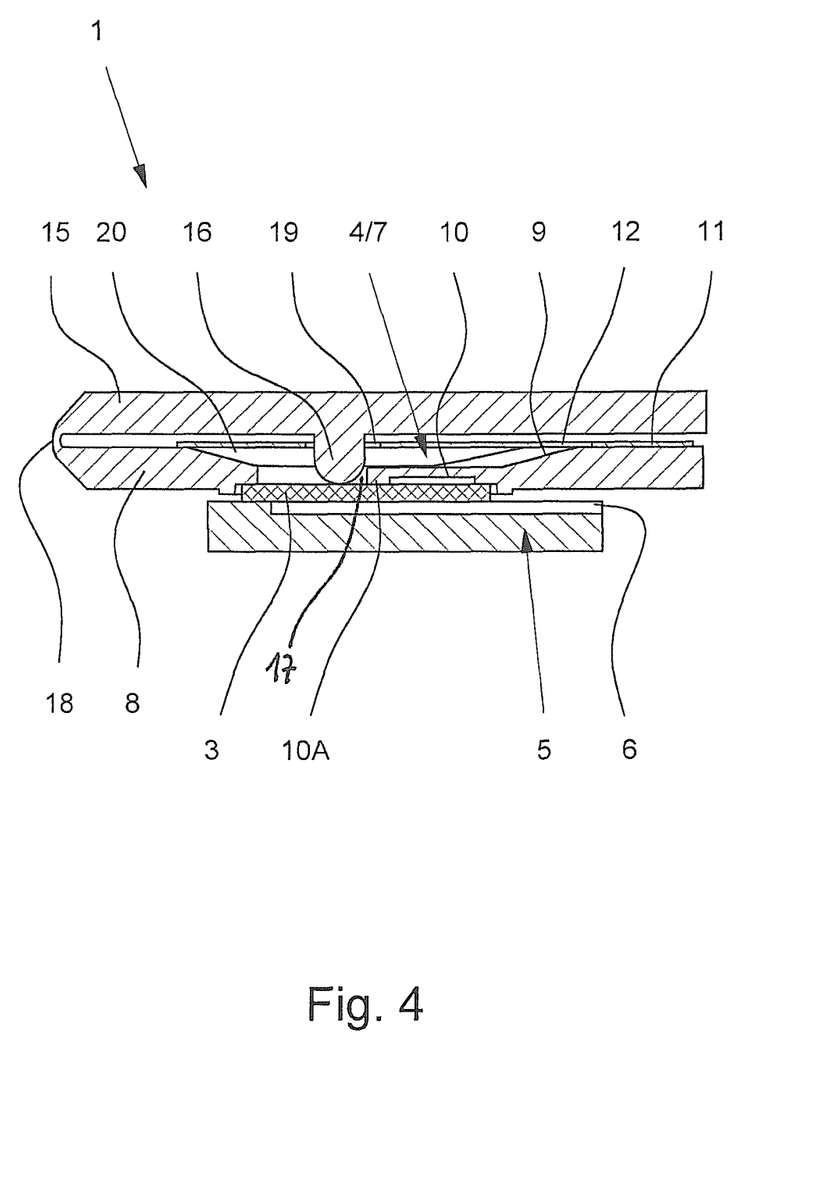
FIG. 4 is a schematic section through the device according to FIG. 3 with the lid closed.

FIG. 3 shows in a schematic section the proposed device 1 according to a second embodiment with an open lid 15 while FIG. 4 shows it in schematic section with the lid 15 closed. In FIGS. 3 and 4 neither the sample fluid 2 nor the chemical 13 is shown for reasons of clarity.

In the second embodiment, the microfluidic connection between the receiving region 7 or guide region 10 on the one hand and the separating device 3 on the other hand has been altered compared with the first embodiment. The fluidic connection is provided here by a guide element 16. The guide element 16 is preferably in the form of a pin-like projection on the lid 15. However, other design solutions are also possible.

After the receiving region 7 has been filled with the sample fluid 2 and after the preferred pre-treatment by dissolving the chemical 13 (not shown), the fluidic connection to the separating device 3 is established by moving the guide element 16 up to it. In the embodiment shown this is done, in particular, by moving or flipping the guide element 16 over or onto the separating device 3 and/or moving it into the vicinity of the receiving region 7 or guide region 10. Particularly preferably, a microfluidic or capillary channel 17 for the sample fluid 2 (not shown) towards the separating device 3 is formed between the guide element 16 and the receiving region 7 or the adjoining guide region 10 or an adjacent wall 10A, as shown in FIG. 4. In the second embodiment, the microfluidic or capillary channel 17 thus forms the fluidic connection.

In both embodiments, the sample fluid 2 is preferably at least primarily conveyed to the separating device 3 by capillary forces.

In the second embodiment, the lid 15 is preferably mounted on the device 1 or carrier 8 so as to be capable of folding over, and is preferably pivotable about a hinge 18 which is preferably in the form of a film hinge. However, other design solutions are also possible.

In the second embodiment the fluidic connection is thus established or opened in particular by flipping over or closing the lid 15 or the device 1.

In the second embodiment, the cover 11 preferably comprises a (second) opening 19, so that the guide element 16 is able to engage in the receiving chamber 20 above the separating device 3 or adjacent to the receiving region 7/guide region 10. However, other design solutions are also possible.

Particularly preferably, the microfluidic or capillary channel 17 is formed between the guide element 16 and the wall 10A, which extends towards the separating device 3—for example at the end or on the edge of the guide region 10—and is optionally supported thereon.

Figure 5:
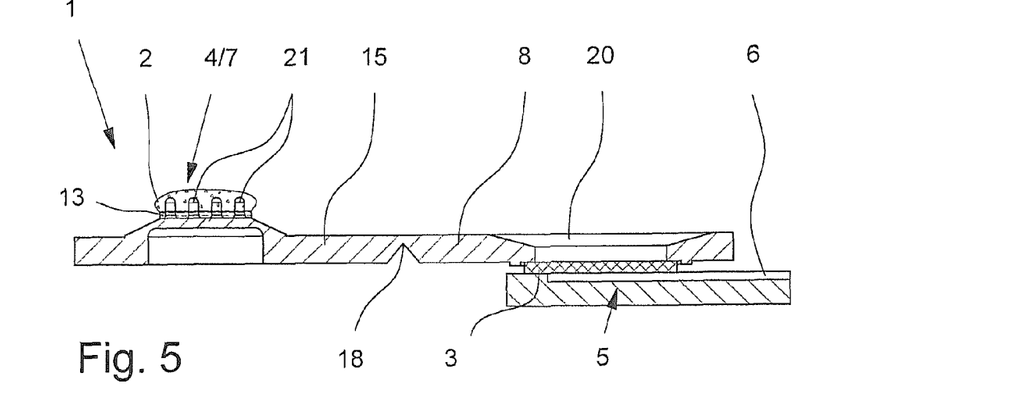
FIG. 5 is a schematic section through a proposed device according to a third embodiment, with the lid open.
Figure 6:
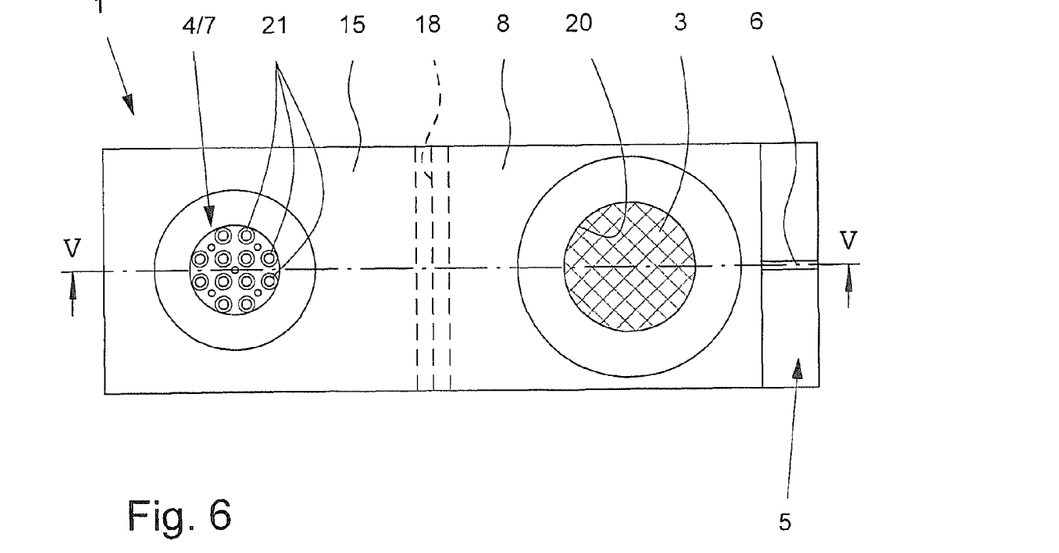
FIG. 6 is a plan view of the device according to FIG. 5.
Figure 7:
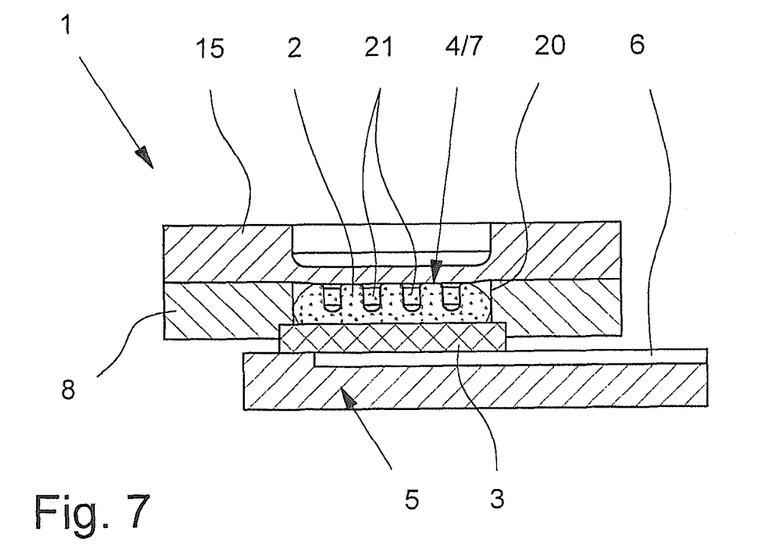
FIG. 7 is a schematic section through the device according to FIG. 5 with the lid closed.

FIG. 5 shows in a schematic section the proposed device 1 according to a third embodiment with the lid 15 open. FIG. 6 shows the device 1 in schematic plan view. FIG. 7 shows the device 1 with the lid 15 closed or with the receiving region 7 arranged on the separating device 1.

In the third embodiment, the receiving region 7 is movable, particularly by folding, over or onto the separating device 3, so as to supply the sample fluid 2 to the separating device 3. In the embodiment shown this is achieved in particular by arranging the receiving device 4 or the receiving region 7 preferably on the lid 15 of the device 1, which in turn is movable, preferably by folding, particularly by means of the hinge 18, over or onto the separating device 3.

The receiving device 4 or the receiving region 7 preferably comprises a retaining or metering structure here, which is particularly preferably formed by a plurality of elevations or columns 21. The elevations or columns 21 are arranged in particular in the manner of a field or form a field of columns. In this way the capillarity is increased in certain areas. Moreover, this provides a way of retaining the sample fluid 2. In particular, it makes metering simple as a user (not shown) can tell when the elevations or columns 21—i.e. the field of columns—are covered by the sample fluid 2, as schematically shown in FIG. 5.

The receiving device 4 or the receiving region 7 is preferably provided with the chemical 13, as shown in FIG. 5. For example, the chemical is provided or dried in at the base of the elevations or columns 21. However, other local arrangements are also possible.

The chemical 13 can preferably be dissolved by the sample fluid 2 very rapidly, in particular within 1 to 2 seconds. Particularly preferably, this takes less than 1 second. Theoretically, the pre-treatment of the sample fluid 2 or the dissolving of the chemical 13 may also take place more slowly or take longer, for example more than 5 seconds and/or optionally one minute or more.

After the filling of the receiving region 7, i.e. the metering of the sample fluid 2, and the preferred pre-treatment by the chemical 13, the receiving region 7 or the pre-treated sample fluid 2 is brought into fluidic contact with the separating device 2, in this case particularly preferably by moving or folding the receiving region 7 over or onto the separating device 3, as shown in FIG. 7.

The receiving region 7 or the sample fluid 2 is thus moved into the receiving chamber 20 over the separating device 3 and brought into fluidic contact with the separating device 3. The sample fluid 2 is able to flow through the separating device 3—particularly by capillary forces—and in this way constituents can be separated from the sample fluid 2.

Figure 8:
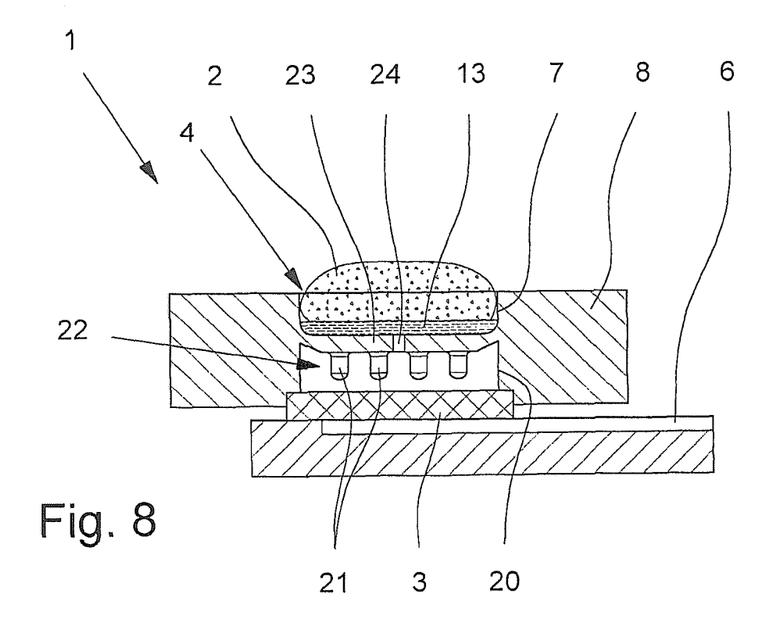
FIG. 8 is a schematic section through a proposed device according to a fourth embodiment.

FIG. 8 shows in schematic section the proposed device 1 according to a fourth embodiment. Here, the receiving device 4 additionally comprises between the receiving region 7 and the separating device 3 an intermediate store 22 which may be formed for example above or in the receiving chamber 20 of the separating device 3.

In the fourth embodiment the receiving region 7 is formed for example by a depression in the carrier 8. The receiving region 7 is preferably separated from the intermediate store 22 by an intermediate wall 23 and/or connected to the intermediate store 22 through a fluidic connection, preferably a throttle connection, which in this case is formed by a bore 24 or the like.

The intermediate store 22 is preferably provided with a metering or retaining structure, particularly made up of a plurality of elevations or columns 21, as shown in FIG. 8. In particular, the elevations or columns 21 project from the intermediate wall 23 and/or are spaced somewhat from the separating element 3. In particular, this ensures that only when it has been at least substantially completely filled with sample fluid 2 does the intermediate store 22 convey the sample fluid 2 to the separating device 3. This is achieved in the embodiment shown by the fact that the sample fluid 2 flowing out of the receiving region 7 through the fluidic connection or bore 24 into the intermediate store 22 is initially retained there between the columns 21 as a result of the capillary forces present, and only once it has been substantially completely filled does the sample fluid 2 come into fluidic contact with the separating device 3. In this way it is possible to gain or ensure additional time for the pre-treatment for the sample fluid 2 before it is supplied to the separating device 3.

In the embodiment shown the chemical 13 is arranged in the receiving region 7, but may alternatively or additionally be arranged in the intermediate store 22.

As shown schematically in FIG. 8, the chemical 13 may if required cover or block the fluidic connection—in this case the bore 24—for discharging the sample fluid 2 from the receiving region 7. In this way it can be ensured that the sample fluid 2 first dissolves the chemical 13 before the sample fluid 2 is able to flow onwards—optionally via the intermediate store 22—to the separating device 3.

The dish-like recess of the receiving region 7 particularly preferred in the fourth embodiment in turn enables easy metering of the sample fluid 2. In fact, a user (not shown) can very easily tell that sufficient sample fluid 2 has been added once the receiving region 7 is totally full. This also makes metering easier.

In the fourth embodiment the separating device 3, the intermediate store 22 and/or the receiving region 7 are preferably arranged one above the other.

Figure 9:
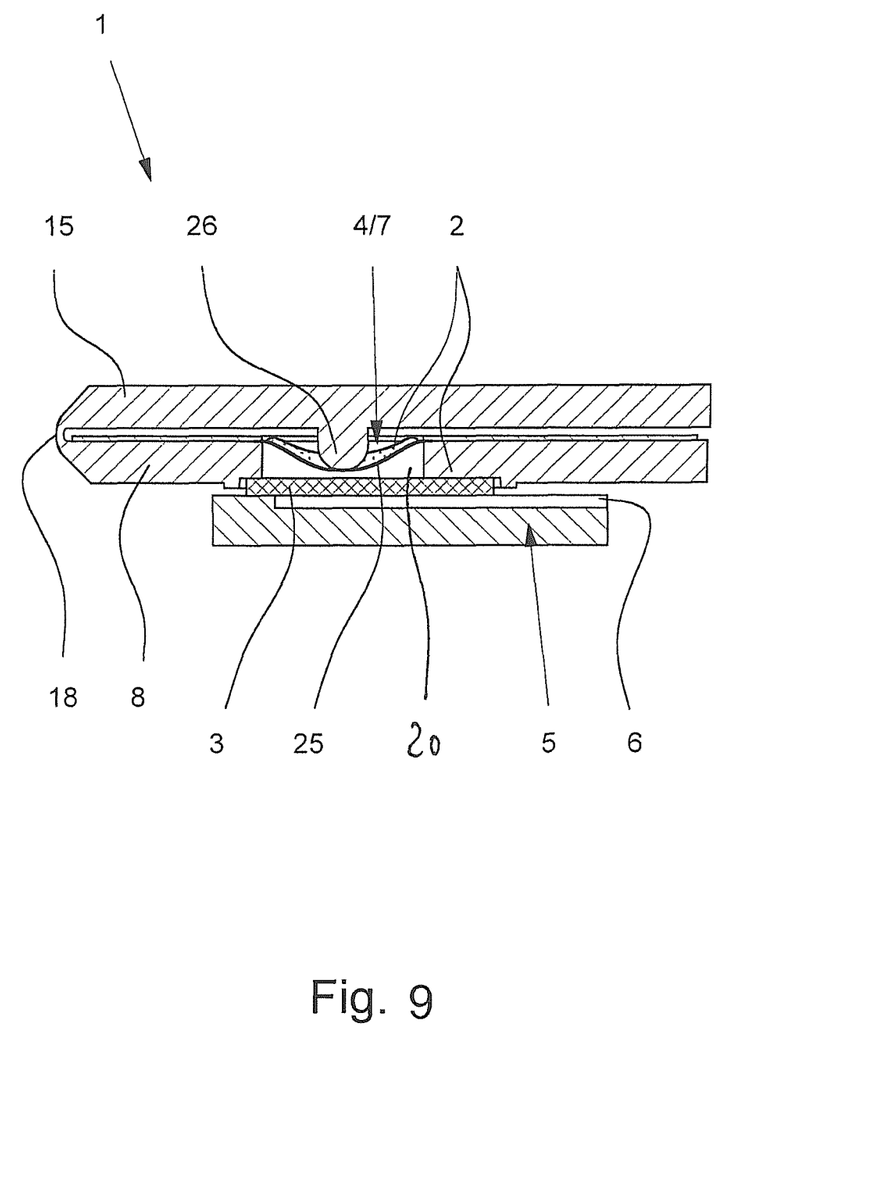
FIG. 9 is a schematic section through a proposed device according to a fifth embodiment.

FIG. 9 shows in schematic section the proposed device 1 according to a fifth embodiment. The receiving device 4 or the receiving region 7 comprises here a deformable deformation region which is formed in particular by a perforated film, membrane 25 or the like. The membrane 25 is preferably held on the carrier 8, for example with a specific pre-tensioning.

The receiving device 4 or the receiving region 7 and/or the deformation region or the membrane 25 may be provided with the chemical 13, which is not shown here, for reasons of simplicity. Once the receiving region 7 has been filled with the sample fluid 2 and correspondingly pre-treated by dissolving the chemical 13, the deformation region or the membrane 25 can be brought into fluidic contact with the separating device 3 by deformation, as shown in FIG. 9. In particular, this can be done by means of a manipulating element 26, which is preferably movable into the receiving region 7 or receiving chamber 20 or towards the separating device 3, in particular by folding over the lid 15, which may if required carry the manipulating element 26, as shown in FIG. 9. However, other design solutions are also possible.

The deformation of the deformation section or of the membrane 25 causes the sample fluid 2 to be brought into fluidic contact with the separating device 3 and enables it to flow onto and through the separating device 3.

It should be noted that individual features and aspects of the various embodiments can be combined with one another as desired, but may also be implemented independently of one another.

LIST OF REFERENCE NUMERALS 1 device
2 sample fluid
3 separating device
4 receiving device
5 structure
6 channel
7 receiving region
8 carrier
9 ramp
10 guide region
10A wall
11 cover
12 receiving opening
13 chemical
14 groove
15 lid
16 guide element
17 capillary channel
18 hinge
19 opening
20 receiving chamber
21 column
22 intermediate store
23 intermediate wall
24 bore
25 membrane
26 manipulating element

The invention claimed is:

1. A device (1) for separating constituents of a sample fluid (2), comprising:
 a receiving device (4) for receiving the sample fluid (2),
 a separating device (3) for separating constituents of the sample fluid (2), the sample fluid (2) being adapted to be supplied to the separating device (3) from the receiving device (4), and
 a structure (5) provided downstream of the separating device (3) for draining the sample fluid (2) after constituents have been separated off,
 wherein the receiving device (4) comprises a receiving region (7) for metering, stopping or delaying the sample fluid (2) by capillary force and/or a chemical (13) that can be dissolved by the sample fluid (2), in order to pre-treat the sample fluid (2) before it is supplied to the separating device (3),
 wherein the receiving region (7) comprises a sloping ramp (9) and an associated cover (11), and a guide region (10) that is arranged at or terminates at a spacing above the separating device (3), which operate to stop or delay the sample fluid (2), and
 wherein the receiving region (7) includes a guide element (16) that is foldable over at least one of the receiving device (4) and the separating device (3) in order to provide a fluidic connection between the receiving region (7) and the separating device (3).

2. The device according to claim 1, wherein the receiving region (7) is foldable over the separating device (3) thereby providing the guide element (16) that is foldable over at least one of the receiving device (4) and the separating device (3) such that the sample fluid (2) can thereby be conveyed towards the separating device (3).

3. The device according to claim 1, wherein the receiving region (7) comprises at least one of a retaining or metering structure having a plurality of columns (21) arranged as a field, for increasing the capillarity in certain areas and/or for metering the sample fluid (2).

4. The device according to claim 1, wherein the receiving device (4) comprises a throttle connection between the receiving region (4) and the separating device (3) for the throttled conveying of sample fluid (2) from the receiving region (7) to the separating device (3).

5. The device according to claim 1, wherein the guide element (16) provides a fluidic connection between the receiving region (7) and the separating device (3) for the sample fluid (2).

6. The device according to claim 5, wherein the guide element (16) forms a capillary channel (17), between itself and a portion or a wall (10A) of the receiving region (7), for conveying the sample fluid (2) to the separating device (3).

7. The device according to claim 1, wherein the receiving device (4) comprises an intermediate store (22) for the sample fluid (2) between the receiving region (4) and the separating device (3), while in particular the receiving device (4) comprises a throttle connection between the receiving region (4) and the intermediate store (22) for the throttled conveying of sample fluid (2) from the receiving region (4) into the intermediate store (22).

8. The device according to claim 7, wherein the receiving region (4), the intermediate store (22) and the separating device (3) are arranged above one another.

9. The device according to claim 1, wherein the receiving region (7) comprises a deformation region formed by a membrane (25), which can be brought into fluidic contact with the separating device (3) by deformation.

10. The device according to claim 1, wherein the chemical (13) contains or is an agglutinating agent.

11. The device according to claim 1, wherein the chemical (13) contains or is a clotting inhibitor.

* * * * *